(12) United States Patent
Demmy et al.

(10) Patent No.: US 8,496,153 B2
(45) Date of Patent: Jul. 30, 2013

(54) ANVIL-MOUNTED DISSECTING TIP FOR SURGICAL STAPLING DEVICE

(75) Inventors: Todd Demmy, East Amherst, NY (US); Lee Ann Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 1403 days.

(21) Appl. No.: 11/729,686

(22) Filed: Mar. 29, 2007

(65) Prior Publication Data

US 2008/0237297 A1     Oct. 2, 2008

(51) Int. Cl.
*A61B 17/064*     (2006.01)
(52) U.S. Cl.
USPC ................ 227/176.1; 227/175.1; 227/180.1; 227/19
(58) Field of Classification Search
USPC ............................ 227/176.1, 180.1, 19, 175.1
See application file for complete search history.

(56) References Cited

U.S. PATENT DOCUMENTS

| | | | |
|---|---|---|---|
| 2,887,111 A * | 5/1959 | Leyro Diaz | 606/148 |
| 5,397,324 A * | 3/1995 | Carroll et al. | 606/139 |
| 5,447,265 A * | 9/1995 | Vidal et al. | 227/176.1 |
| 5,665,100 A | 9/1997 | Yoon | |
| 5,728,110 A | 3/1998 | Vidal et al. | |
| 5,772,099 A * | 6/1998 | Gravener | 227/176.1 |
| 5,816,471 A * | 10/1998 | Plyley et al. | 227/178.1 |
| 6,704,210 B1 * | 3/2004 | Myers | 361/773 |
| 2004/0094597 A1 * | 5/2004 | Whitman et al. | 227/180.1 |
| 2004/0243151 A1 * | 12/2004 | Demmy et al. | 606/139 |
| 2005/0119669 A1 * | 6/2005 | Demmy | 606/139 |
| 2005/0216055 A1 * | 9/2005 | Scirica et al. | 606/219 |
| 2006/0016853 A1 | 1/2006 | Racenet | |
| 2006/0168531 A1 | 7/2006 | Sato | |

OTHER PUBLICATIONS

European Search Report for EP 08 251159.3-1526 date of completion is Oct. 28, 2008 (9 pages).
European Search Report for Application No. 08251159.3-1526/1974677 dated Nov. 11, 2008.

* cited by examiner

*Primary Examiner* — Michelle Lopez

(57) ABSTRACT

A surgical stapling device including a handle assembly, an endoscopic portion and an end effector is disclosed. The endoscopic portion extends distally from the handle assembly and defines a first longitudinal axis. The end effector defines a second longitudinal axis and includes an anvil assembly and a cartridge assembly. The anvil assembly is supported adjacent a distal end of the endoscopic portion and includes a dissecting tip extending therefrom. The cartridge assembly is pivotably mounted adjacent the distal end of the endoscopic portion. The cartridge assembly is mounted for pivotal movement in relation to the anvil assembly between open and approximated positions.

20 Claims, 7 Drawing Sheets

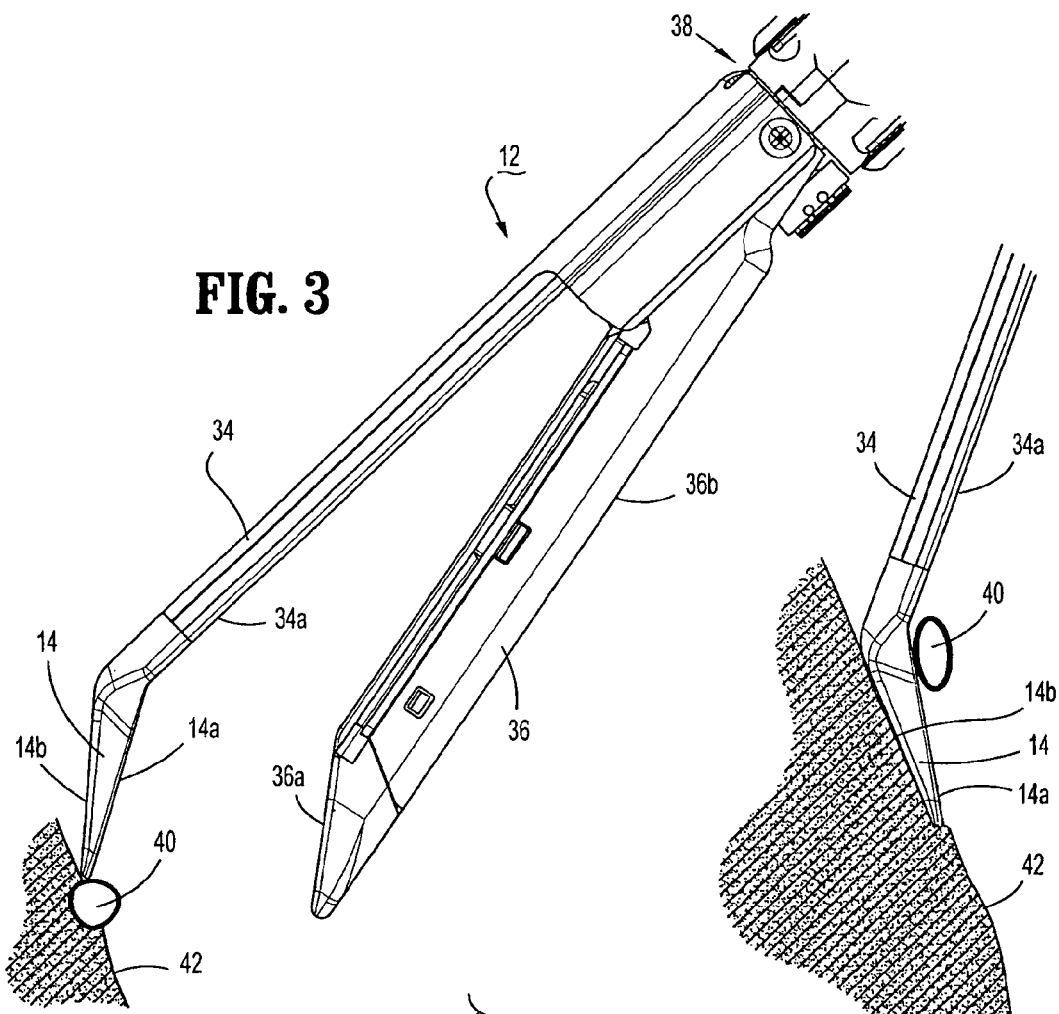
FIG. 3
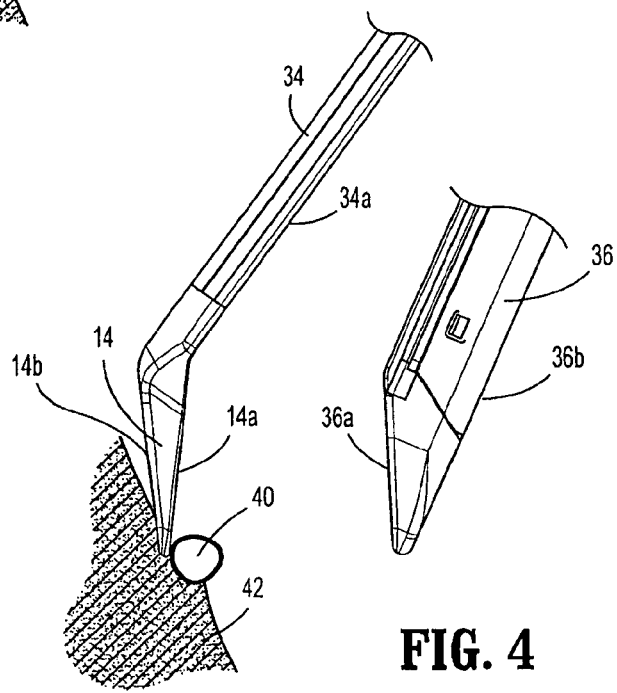
FIG. 5
FIG. 4

ANVIL-MOUNTED DISSECTING TIP FOR SURGICAL STAPLING DEVICE

CROSS REFERENCE TO RELATED APPLICATIONS

This application is a continuation-in-part of U.S. application Ser. No. 11/784,115, filed Apr. 5, 2007, which is a continuation application of U.S. application Ser. No. 11/030,527, filed Jan. 6, 2005, which is a divisional of U.S. application Ser. No. 10/764,103, filed Jan. 23, 2004, which claims priority from U.S. Provisional Application Ser. No. 60/466,378, filed Apr. 29, 2003, and a continuation-in-part of U.S. application Ser. No. 10/835,543, filed Apr. 29, 2004 which also claims priority from U.S. Provisional Application Ser. No.60/466,378, filed Apr. 29, 2003. Each of the foregoing applications are incorporated herein in their entirety by reference.

BACKGROUND

1. Technical Field

This application relates to a surgical stapling device. More particularly, this application relates to a surgical stapling device having an improved tip construction for dissecting and/or separating tissue.

2. Related Art

Surgical stapling or fastener-applying devices for joining tissue are well known. Typically, such devices include opposing jaw structure for grasping and clamping selected tissue, wherein one of the jaws of the opposing jaw structure includes a cartridge which houses a plurality of staples or fasteners and the other jaw includes an anvil for formation of the fastener. In some instruments, a knife is provided to cut tissue which has been joined by the staples or fasteners.

Linear surgical stapling devices, for example, include two elongated jaw members which are relatively moveable to capture or clamp tissue. Typically one of the jaw members includes a cartridge which houses a plurality of staples arranged in two or more linear rows and the other member includes an anvil having a plurality of staple forming pockets for receiving and forming the legs of the staples. A knife is often movably positioned between the linear rows of staples such that when the stapling device is positioned about tissue and actuated, the tissue is joined and/or simultaneously or nearly simultaneously cut. Often, a surgical device separate from the stapling device is used to dissect or separate certain adherent tissue from target tissue before the target tissue and/or the certain adherent tissue is operated upon. These procedures require extra steps and devices and can be time consuming and expensive especially during endoscopic procedures.

Accordingly, a continuing need exists in the art for a device which can be used not only to join and cut tissue but also to separate or dissect tissue, e.g., when the jaw members are in an open position.

SUMMARY

The present disclosure relates to a surgical stapling device including a handle assembly, an endoscopic portion and an end effector. The endoscopic portion extends distally from the handle assembly and defines a first longitudinal axis. The end effector defines a second longitudinal axis and includes an anvil assembly and a cartridge assembly. The anvil assembly is supported adjacent a distal end of the endoscopic portion and includes a dissecting tip extending therefrom. The cartridge assembly is pivotably mounted adjacent the distal end of the endoscopic portion and is mounted for pivotal movement in relation to the anvil assembly between open and approximated positions.

The present disclosure also relates to a disposable loading unit for use with a surgical stapling device. The disposable loading unit includes a proximal body portion and an end effector. The proximal body portion is configured for attachment to a portion of the surgical stapling device and defines a first longitudinal axis. The end effector is attached to a distal portion of the proximal body portion and defines a second longitudinal axis. The end effector includes an anvil assembly and a cartridge assembly. The anvil assembly includes a dissecting tip. The cartridge assembly is mounted for movement with respect to the anvil assembly between an open position and an approximated position.

BRIEF DESCRIPTION OF THE DRAWINGS

The accompanying drawings, which are incorporated in and form part of the specification, illustrate the present disclosure when viewed with reference to the description, wherein:

FIG. 3 is a side view of the end effector and of the dissecting tip of the surgical stapling device shown in FIG. 1 with the end effector in the open position adjacent target tissue and certain tissue which is adhered to the target tissue;

FIG. 4 is a side view of a portion of the end effector shown in FIG. 3 with the dissecting tip positioned with respect to the target tissue;

FIG. 5 is a side view of the anvil assembly and dissecting tip shown in FIG. 4 positioned between the target tissue and adjacent tissue;

DETAILED DESCRIPTION

Figure 1:
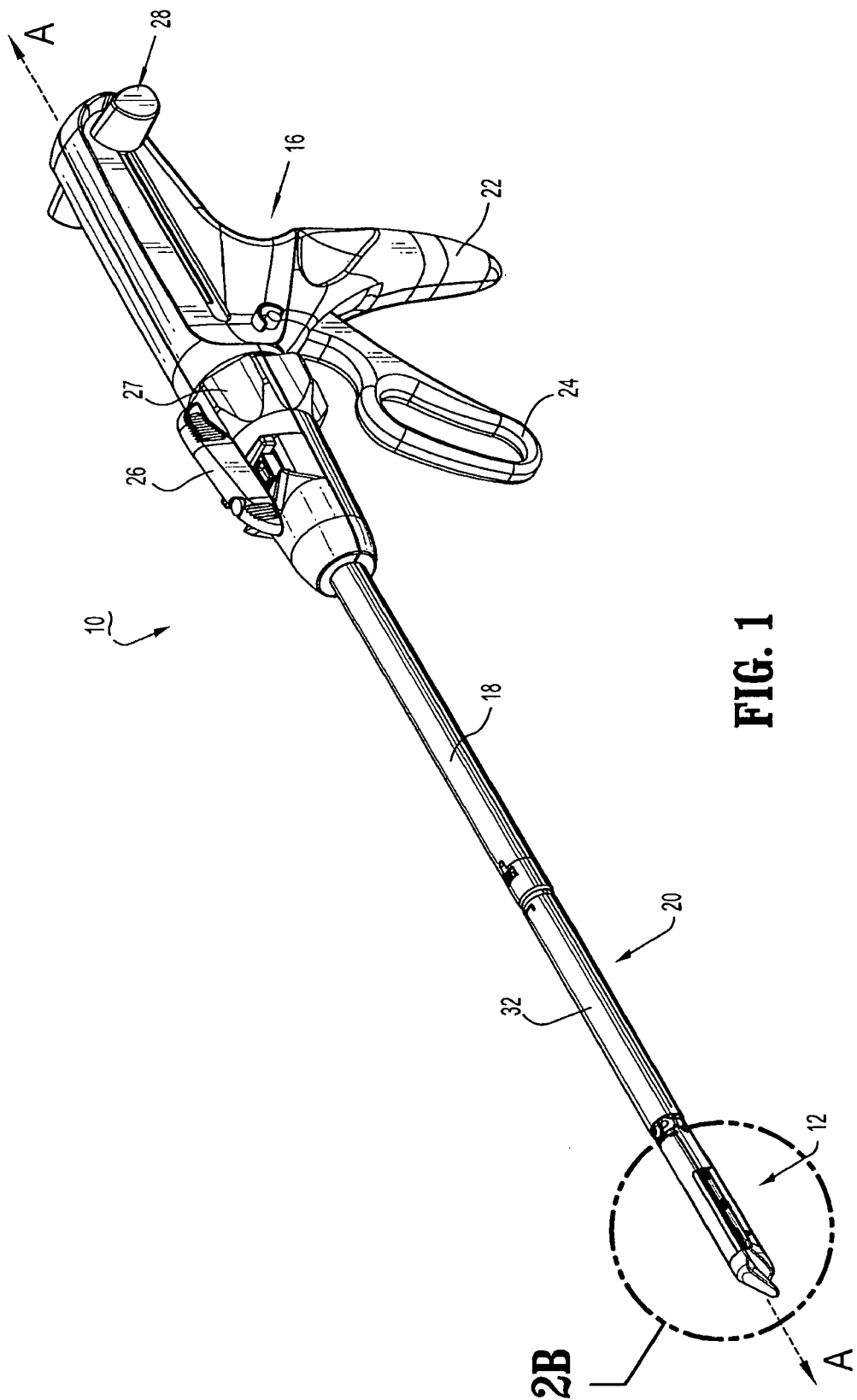
FIG. 1 is a perspective view of a surgical stapling device including one embodiment of the presently disclosed dissecting tip attached to an end effector thereof.

Embodiments of the presently disclosed surgical stapling device having an anvil-mounted dissecting tip are described in detail with reference to the drawings, in which like reference numerals designate identical or corresponding elements in each of the several views. As used herein the term "distal" refers to that portion of the surgical stapler, or component thereof, farther from the user while the term "proximal" refers to that portion of the surgical stapler or component thereof, closer to the user.

Figure 1A:
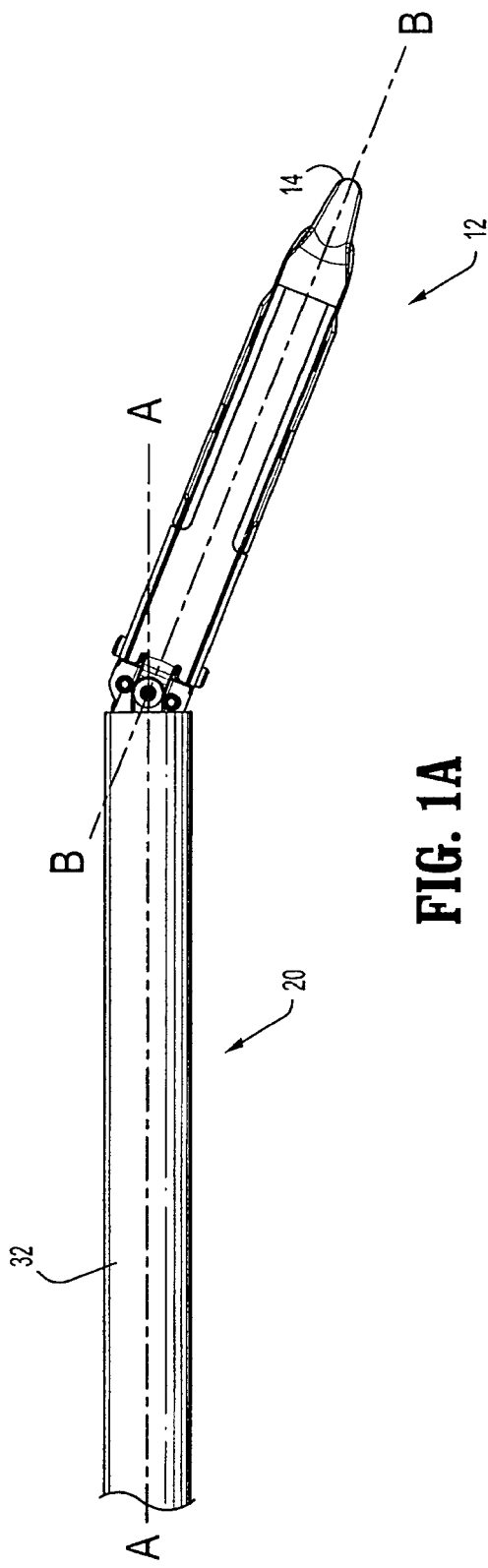
FIG. 1A is a plan view of a portion of the end effector shown in FIG. 1 and illustrates the end effector in an articulated position.

FIG. 1 illustrates a linear surgical stapling device shown generally as reference number 10 including an end effector 12 having a dissecting tip, generally designated as number 14, supported thereon. Surgical stapling device 10 also includes a handle assembly 16 and an endoscopic portion 18, endoscopic portion 18 defining longitudinal axis A-A (FIGS. 1 and 1A). End effector 12 defines a second longitudinal axis B-B (FIG. 1A) and may form part of a disposable loading unit (DLU) or single use loading unit (SULU) 20. Many components of surgical stapling device 10 are substantially as described in U.S. Pat. Nos. 5,865,361, 6,079,606, 6,241,139, 6,330,965 and 6,669,073, which are incorporated herein in their entirety by reference. It is contemplated that the presently disclosed embodiments of dissecting tip 14 may be used in association with other known linear stapling devices of both endoscopic and open construction. These devices include articulating and non-articulating devices as well as reusable and non-reusable devices. Examples of such devices are disclosed in U.S. Pat. Nos. 6,202,914, 6,250,532, 6,109,500, 6,032,849, 5,584,425, 5,571116, 5,413,268, 5,312,023, 5,505,363, 5,540,375, 5,554,169, 5,507,426, 5,482,197, which are also incorporated herein in their entirety by reference. Various embodiments of dissecting tips 14 along with end effectors 12 having an anvil assembly 34 that is stationary with respect to a movable cartridge assembly 36 are discussed in detail in this application.

FIGS. 1-9 illustrate embodiments of the presently disclosed dissecting tip 14 in combination with surgical stapling device 10. As discussed above, surgical stapling device 10 includes a handle assembly 16, an elongated body or endoscopic portion 18, and an end effector 12. Briefly, handle assembly 16 is shown including a stationary grip member 22, a pivotable trigger 24, an articulation lever 26, a rotation knob 27 and return knob 28. In accordance with various embodiments, SULU 20 (and/or DLU) is adapted to be releasably attached to elongated body portion 18 and includes a proximal body portion 32 and end effector 12. End effector 12 is pivotally attached to proximal body portion 32, which is pivotably attached to end effector 12 for articulation of end effector 12 in relation to proximal body portion 32 (see FIG. 1A), in accordance with a disclosed embodiment.

End effector 12 includes an anvil assembly 34 and a cartridge assembly 36 which houses a plurality of linear rows of staples. Anvil assembly 34 and cartridge assembly 36 are pivotal in relation to each other between an open position and a clamped or approximated position. Pivotable trigger 24 is actuable through an actuation stroke or strokes to move cartridge assembly 36 in relation to anvil assembly 34 between the open position and the clamped position and to eject staples from cartridge assembly 36.

An example of various aspects of the present disclosure, including actuation of a surgical stapling apparatus, is disclosed in commonly-owned U.S. Pat. No. 6,953,139 to Milliman et al. (the '139 patent), the entire contents of which are hereby incorporated by reference herein.

Figure 2A:
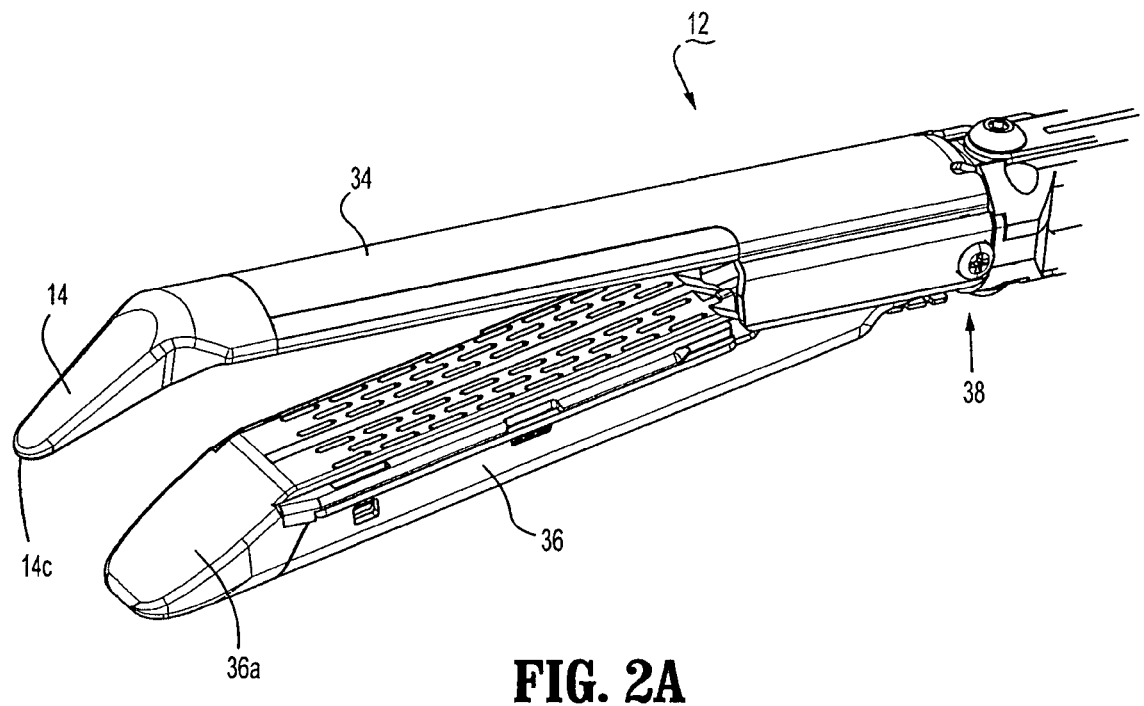
FIG. 2A is an enlarged view of the end effector in an open position.
Figure 2B:
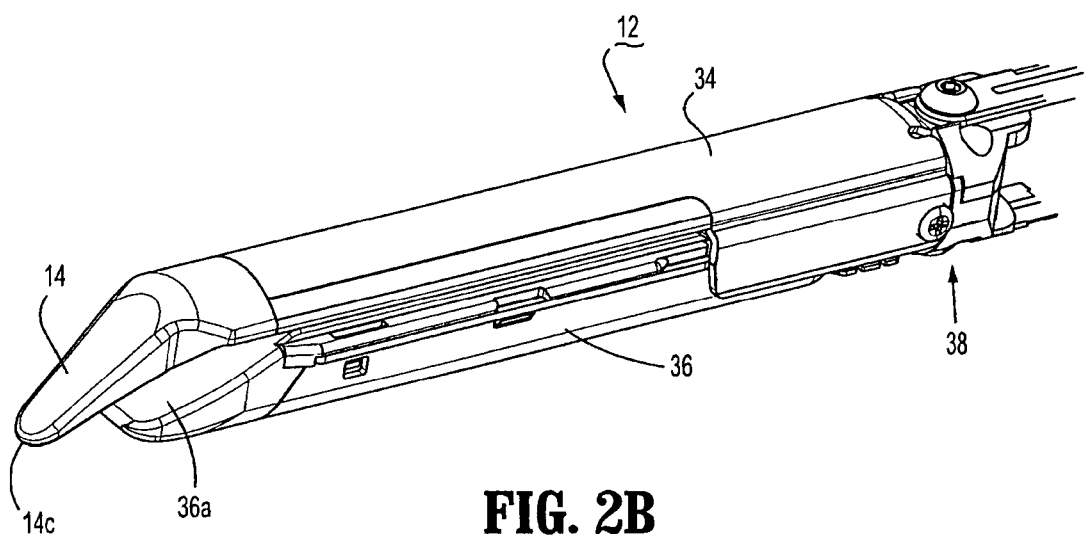
FIG. 2B is an enlarged view of the indicated area of detail shown in FIG. 1 and illustrates the end effector in a closed position.

Dissecting tip 14 is secured to a distal end of the end effector 12. Alternately, dissecting tip 14 may be integrally formed with end effector 12, or end effector 12 and dissecting tip 14 may be of monolithic construction. In an embodiment, dissecting tip 14 is secured to a distal surface of anvil assembly 34 which is contiguous with a tissue contact surface 34a of anvil assembly 34. Dissecting tip 14 may be formed from a surgical grade metal or plastic and is attached to anvil assembly 34 using any known suitable fastening technique, e.g., adhesives, welding, soldering, brazing, pins, etc. Alternately, other known surgically approved materials may be used to construct dissecting tip 14. In this embodiment, dissecting tip 14 may include a smooth inner surface 14a, a smooth outer surface 14b (FIGS. 3-6) and a rounded thin blunt tip 14c (FIGS. 2A and 2B). The curved surface can be formed with any suitable radius. A one inch radius has been found suitable for certain applications. Inner surface 14a may be curved and formed by plural curved radii. Smooth surfaces may help prevent dissecting tip 14 from snagging, pulling and/or cutting tissue. Inner surface 14a of dissecting tip 14 extends downwardly towards cartridge assembly 36 to a location beyond the distal end of cartridge assembly 36. By extending dissecting tip 14 beyond cartridge assembly 36, access to adjacent tissue is improved. In addition, visualization of dissecting tip 14 to confirm proper position and that dissection of adhered tissue 40 is completed is also improved.

In the illustrated embodiments, the width of dissecting tip 14 generally decreases from its proximal end to its distal end and at its greatest width is substantially equal to or smaller than the width of cartridge assembly 36. It is envisioned that there are substantially smooth blends or transitions from dissecting tip 14 to the portion(s) of the jaw structure to which dissecting tip 14 is secured or from which it extends. When anvil assembly 34 and cartridge assembly 36 are in the clamped or approximated position, dissecting tip 14 is spaced from a distal angled surface 36a of cartridge assembly 36. The space therebetween is generally at least the same, or preferably greater, e.g., about two times greater, than the gap between the tissue contacting surfaces of anvil assembly 34 and cartridge assembly 36 when they are approximated. However, there may be instances when it is desired to have less space between dissecting tip 14 and distal angled surface 36a of cartridge assembly 36, for example when it is desired to compress tissue in that location.

Other features of dissecting tip 14 in connection with surgical stapling device 10 are disclosed in commonly-owned U.S. Publication Nos. 2004/0243151 and 2005/0119669, the entire contents of which are hereby incorporated by reference herein.

Referring now to FIGS. 3-5, when surgical stapling device 10 is used to dissect certain tissue 40, e.g., blood or airway vessels, from target tissue 42, e.g., stomach, lung, etc., an outer surface 14a (e.g., straight or curved) of dissecting tip 14 can be pressed or passed against target tissue 42 and slid behind certain tissue 40, e.g., adherent tissue, to separate and/or dissect tissue 40 from, for example, adherence with target tissue 42.

In a particular embodiment, positioning dissecting tip 14 behind certain tissue 40 may be accomplished with anvil assembly 34 and cartridge assembly 36 in an open (including a partially open) position. Such positioning of dissecting tip 14 when anvil assembly 34 and cartridge assembly 36 are in an open position is facilitated by dissecting tip 14 being disposed on anvil assembly 34 and by anvil assembly 34 being fixed from movement with respect to cartridge assembly 36. Further, with the exception of articulation of end effector 12 with respect to endoscopic portion 18 (as discussed below), anvil assembly 34 is fixed from movement with respect to endoscopic portion 18. As such, the tasks of positioning dissecting tip 14 at a particular location, piercing and/or penetrating tissue, maneuvering around and/or within tissue, and/or removing/dissecting tissue 40 from target tissue 42 are more easily accomplished with surgical stapling device 10 having dissecting tip 14 extending from an anvil assembly 34 that is fixed with respect to cartridge assembly 36 vis-à-vis having dissecting tip 14 extending from a movable anvil assembly. More specifically, anvil assembly 34 is rigidly connected to a pivot 38 and cartridge assembly 36 is pivotably connected to pivot 38. Accordingly, end effector 12 can pivot with respect to endoscopic portion 18.

Moreover, dissecting tip 14 of the present disclosure functions as an extension of endoscopic portion 18, such that motion of endoscopic portion 18 is directly transferred to anvil assembly 34 and to dissecting tip 14 (when end effector 12 is in a non-articulated position). By contrast, a dissecting tip 14 disposed adjacent a distal end of a movable jaw member (with respect to opposing jaw member and endoscopic portion 18) may be harder to control when end effector 12 is in an open position, as motion of endoscopic portion 18 is not directly transferred to dissector tip 14 because its associated jaw member lacks a fixed rigidity with respect to opposing jaw member and endoscopic portion 18.

Alternately, cartridge assembly 36 can be moved to the clamped or approximated position during dissection of tissue. Thereafter, either or both of tissue 40 and target tissue 42 can be independently joined and/or cut by clamping and actuating surgical stapling device 10.

It is noted that although not described in detail, end effector 12 may be adapted to access the surgical site through a trocar cannula assembly as is known in the art. To accomplish this, anvil assembly 34 and cartridge assembly 36 are maintained in a clamped or approximated position as endoscopic portion 18 and end effector 12 are inserted through a cannula (not shown). For facilitation of such use, it is envisioned that dissecting tip 14 does not extend below a plane defined by a bottom surface 36b of cartridge assembly 36, nor does dissecting tip 14 extend outwardly beyond the sidewalls of cartridge assembly 36. As such, surgical stapling device 10 including dissecting tip 14 may be used with a trocar cannula assembly sized to receive a surgical stapling device not having a dissecting tip 14.

Figure 6:
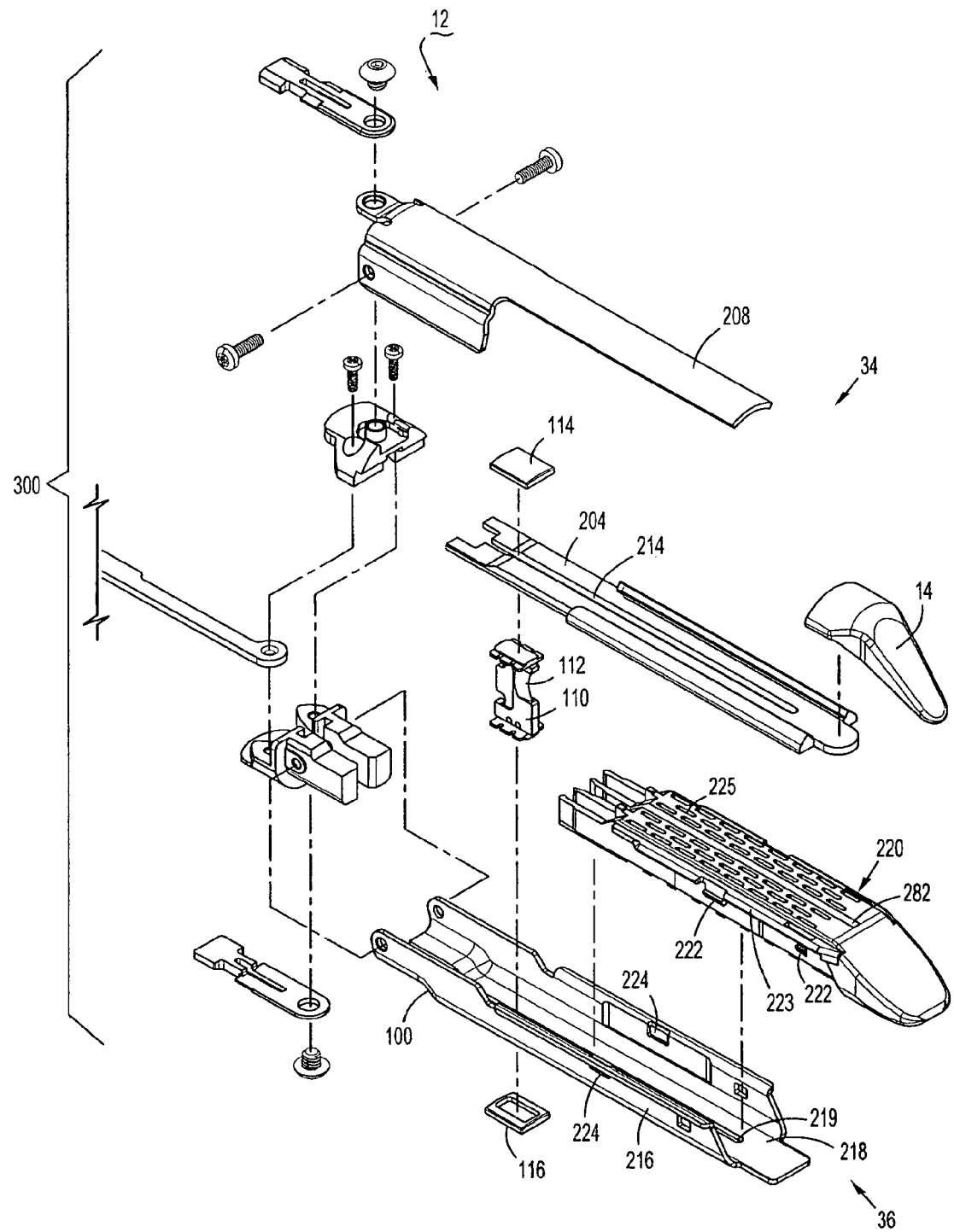
FIG. 6 is an exploded view of the end effector in accordance with embodiments of the present disclosure.

Now referring to FIG. 6, an exploded view of end effector 12 is illustrated in accordance with an embodiment of the present disclosure. Anvil assembly 34 includes an anvil portion 204 having a plurality of staple deforming concavities and a cover plate 208 secured to a top surface of anvil portion 204 to define a cavity therebetween. Cover plate 208 is provided to help prevent pinching of tissue during clamping and firing of surgical stapling device 10. The cavity is dimensioned to receive an upper portion 114 of a closure apparatus 110. A longitudinal slot 214 extends through anvil portion 34 to facilitate movement of closure apparatus 110.

Cartridge assembly 36 includes a carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. Support channel 218 includes a longitudinal slot 219 to facilitate passage of closure apparatus 110, with a lower portion 116 of closure apparatus 110 traveling below elongated channel support 218. A pair of support struts 223 formed on staple cartridge 220 are positioned to rest on side walls of carrier 216 to further stabilize staple cartridge 220 within support channel 218. A camming surface 100 is formed on cartridge assembly 36 and is positioned to engage closure apparatus 110 to facilitate clamping of tissue. That is, when closure apparatus 110 contacts camming surface 100, cartridge assembly 36 is moved towards anvil assembly 34, further details of which are described below.

Staple cartridge 220 also includes retention slots 225 for receiving a plurality of fasteners and/or pushers. A central longitudinal slot 282 extends along the length of staple cartridge 220 to facilitate passage of a knife blade 112 (shown as a part of closure apparatus 110). An example of an articulation mechanism 300 is also shown in accordance with an embodiment of the present disclosure. Further details of articulation mechanism 300 are described in U.S. Pat. No. 6,953,139, which has been incorporated by reference hereinabove, and U.S. patent application Ser. No. 11/544,518, filed on Oct. 6, 2006, the disclosure of which is hereby incorporated by reference herein.

It is further envisioned that a positioning structure is included on surgical stapling device 10 to maintain end effector 18 in a non-articulated position (i.e., substantially aligned with longitudinal axis A-A). An example of such a structure is disclosed in U.S. patent application Ser. No. 11/544,518, which has been incorporated by reference hereinabove. It is contemplated that positioning structure forms a mechanical link adjoining a distal end of endoscopic portion 18 and a portion of end effector 12 (e.g., anvil assembly 34). Additionally, the positioning structure may include first element disposed adjacent the distal end of endoscopic portion 18 that is biased towards a mating second element disposed on end effector 12 (e.g., a spring-biased finger disposed on endoscopic portion 18 and a mating element having at least one finger-receiving groove disposed on end effector 12).

Figure 7:
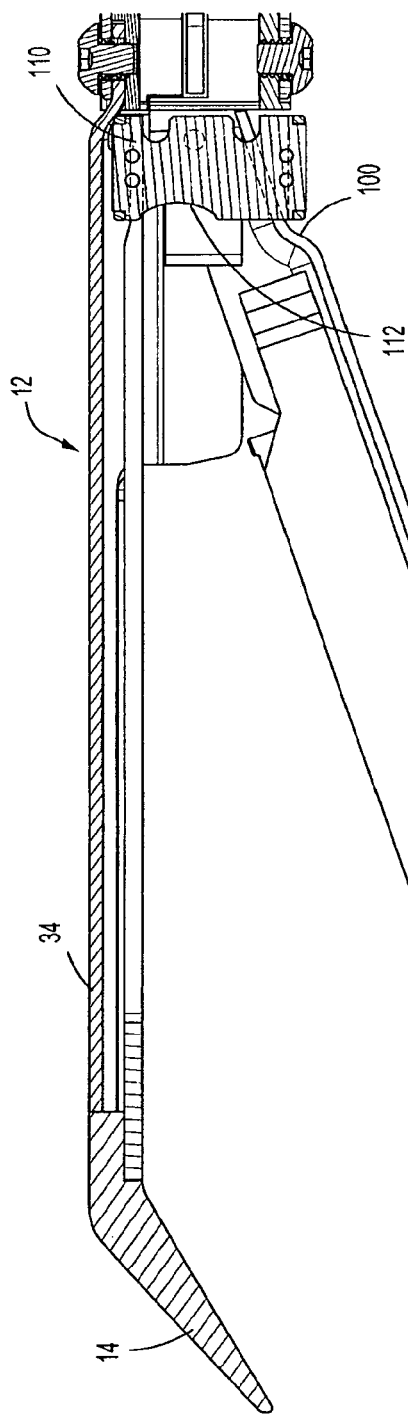
FIGS. 7-9 are side views of the end effector showing a cartridge assembly spaced apart from an anvil assembly, the cartridge assembly closer to the anvil assembly, and the cartridge assembly approximated with the anvil assembly, in accordance with embodiments of the present disclosure.
Figure 8:
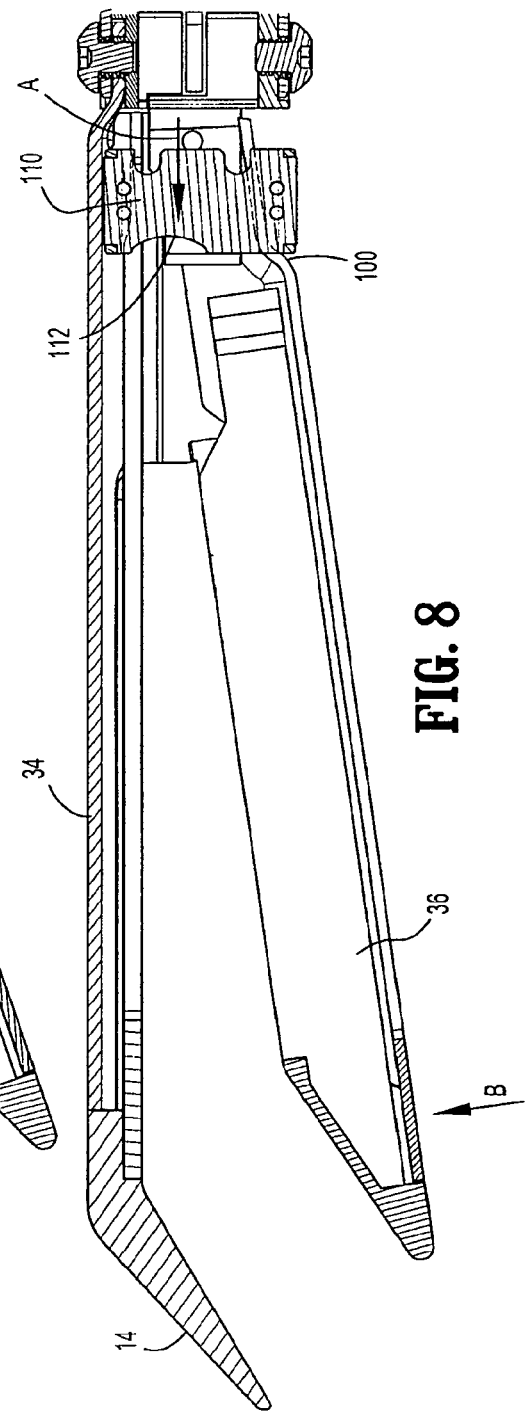
Figure 9:
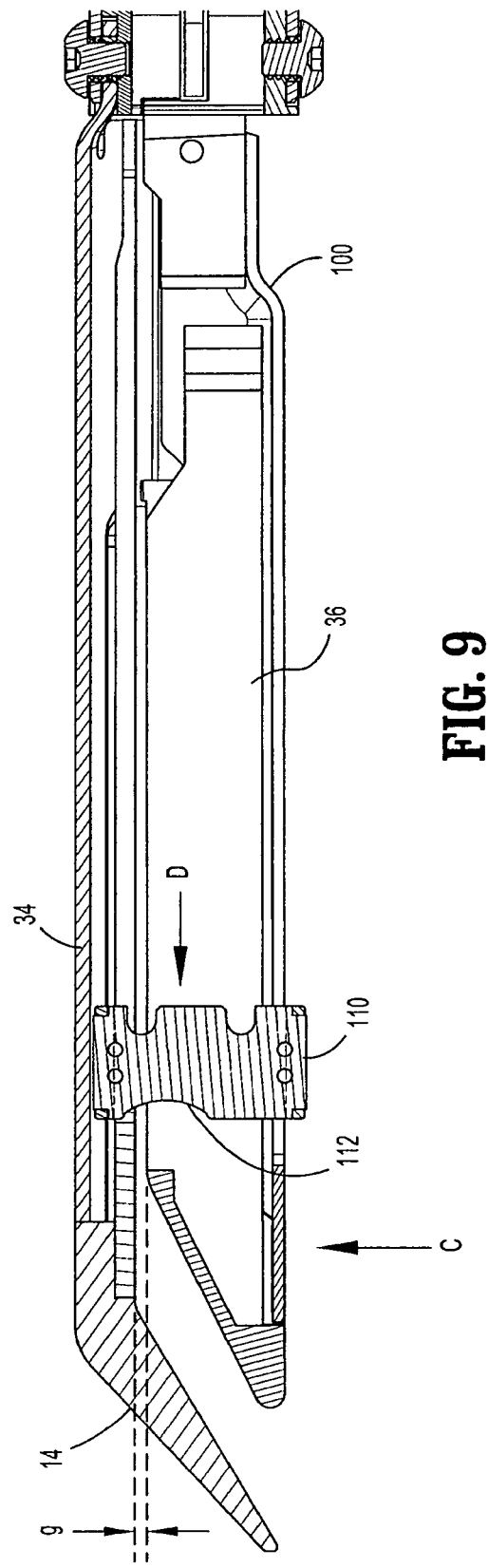

In operation and with reference to FIGS. 6-9, closure apparatus 110 (shown including knife 112) is initially disposed proximally of camming surface 100, when end effector 12 is in an open position (FIG. 7). As closure apparatus 110 advances distally in the direction of arrow A and contacts camming surface 100 of cartridge assembly 36, cartridge assembly 36 moves towards anvil assembly 34 in the direction of arrow B (FIG. 8). Upon continued distal movement of closure apparatus 110, closure apparatus 110 passes camming surface 100, which moves cartridge assembly 36 closer to anvil assembly 34 in the direction of arrow C, and closure apparatus 110 moves in the direction of arrow D towards a distal portion of end effector 12 (FIG. 9). It is also envisioned that closure apparatus 110 maintains a gap "g" between anvil assembly 34 and cartridge assembly 36.

It will be understood that various modifications may be made to the embodiments disclosed herein. For example, each of the dissecting tips may be monolithically or integrally formed with the anvil assembly. Moreover, the size, angles and/or curves of the dissecting tip and/or its surface(s) may be modified to better suit a particular surgical procedure. Therefore, the above description should not be construed as limiting, but merely as exemplifications of various embodiments. Those skilled in the art will envision other modifications within the scope and spirit of the claims appended hereto.

What is claimed is:

1. A surgical stapling device, comprising:
a handle assembly;
an endoscopic portion extending distally from the handle assembly and defining a first longitudinal axis; and
an end effector defining a second longitudinal axis, the end effector including:
an anvil assembly supported adjacent a distal end of the endoscopic portion and including a dissecting tip having an inner surface extending therefrom;
a cartridge assembly pivotally mounted adjacent the distal end of the endoscopic portion and being mounted for pivotal movement in relation to the anvil assembly between open and approximated positions, wherein the anvil assembly is fixed from movement with respect to the cartridge assembly, and wherein a distal-most end of the dissecting tip extends distally beyond a distal-most end of the cartridge assembly, the inner surface of the dissecting tip extending toward the cartridge assembly.

2. The surgical stapling device of claim 1, wherein at least a portion of the dissecting tip is substantially aligned with the first longitudinal axis when the cartridge assembly is in the open position.

3. The surgical stapling device of claim 1, wherein the dissecting tip is fixed from movement with respect to the cartridge assembly when the cartridge assembly is in the open position.

4. The surgical stapling device of claim 1, wherein the end effector is movable from a first position in which the second longitudinal axis is substantially aligned with the first longitudinal axis to at least a second position in which the second longitudinal axis is disposed at an angle to the first longitudinal axis.

5. The surgical stapling device of claim 1, wherein the dissecting tip tapers from a first width at a proximal portion to a second width at a distal portion and wherein the first width is wider than the second width.

6. The surgical stapling device of claim 1, wherein the dissecting tip is configured to puncture tissue.

7. The surgical stapling device of claim 1, wherein the cartridge assembly includes a camming surface thereon.

8. The surgical stapling device of claim 1, wherein a proximal portion of the dissecting tip is integral with a portion of the anvil assembly.

9. The surgical stapling device of claim 1, wherein a proximal portion of the dissecting tip is affixed to a portion of the anvil assembly.

10. The surgical stapling device of claim 1, wherein an inner facing surface of the dissecting tip is substantially parallel to a portion of the cartridge assembly.

11. The surgical stapling device of claim 1, wherein an inner facing surface of the dissecting tip is angled distally downward towards the cartridge assembly.

12. A disposable loading unit for use with an endoscopic surgical stapling device, the disposable loading unit comprising:
   a proximal body portion configured for attachment to a portion of the surgical stapling device, the proximal body portion defining a first longitudinal axis; and
   an end effector attached to a distal portion of proximal body portion, the end effector defining a second longitudinal axis and the end effector including:
      an anvil assembly including a dissecting tip, an inner facing surface of the dissecting tip being angled distally downward towards the cartridge assembly; and
      a cartridge assembly mounted for movement with respect to the anvil assembly between an open position and an approximated position, wherein the anvil assembly is fixed from movement with respect to the cartridge assembly.

13. The disposable loading unit of claim 12, wherein the end effector is pivotably attached to the proximal body portion.

14. The disposable loading unit of claim 12, wherein at least a portion of the dissecting tip is substantially aligned with the first longitudinal axis when the cartridge assembly is in the open position.

15. The disposable loading unit of claim 12, wherein the dissecting tip is fixed from movement with respect to the cartridge assembly when the cartridge assembly is in the open position.

16. The disposable loading unit of claim 12, wherein the end effector is movable from a first position in which the second longitudinal axis is substantially aligned with the first longitudinal axis to at least a second position in which the second longitudinal axis is disposed at an angle to the first longitudinal axis.

17. The disposable loading unit of claim 12, wherein the cartridge assembly includes a camming surface thereon.

18. The disposable loading unit of claim 12, wherein a proximal portion of the dissecting tip is affixed to a portion of the anvil assembly.

19. The disposable loading unit of claim 12, wherein the inner facing surface of the dissecting tip is substantially parallel to a portion of the cartridge assembly.

20. The disposable loading unit of claim 12, wherein a distal-most end of the dissecting tip extends distally beyond a distal-most end of the cartridge assembly.

* * * * *